US00PP29271P3

(12) United States Plant Patent
Li

(10) Patent No.: US PP29,271 P3
(45) Date of Patent: May 1, 2018

(54) LAVENDER PLANT NAMED 'KLELV15115'

(50) Latin Name: *Lavandula stoechas*
Varietal Denomination: KLELV15115

(71) Applicant: Klemm+Sohn GmbH & Co. KG, Stuttgart (DE)

(72) Inventor: Ruijun Li, North Parramatta (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days. days.

(21) Appl. No.: 15/731,048

(22) Filed: Apr. 10, 2017

(65) Prior Publication Data

US 2018/0014448 P1 Jan. 11, 2018

(30) Foreign Application Priority Data

Jul. 5, 2016 (QZ) ..... PBR 2016/1699

(51) Int. Cl.
*A01H 5/02* (2018.01)

(52) U.S. Cl.
USPC ..... Plt./445
CPC ..... *A01H 5/02* (2013.01)

(58) Field of Classification Search
USPC ..... Plt./445
CPC ..... A01H 5/02
See application file for complete search history.

*Primary Examiner* — Kent L Bell
(74) *Attorney, Agent, or Firm* — Bethany R. Roahrig; James M. Weatherly; Cochran Freund & Young LLC

(57) ABSTRACT

A new lavender plant particularly distinguished by dark purple terminal bracts, and very early flowering, is disclosed.

1 Drawing Sheet

Genus and species: *Lavandula stoechas.*
Variety denomination: 'KLELV15115'.

CROSS-REFERENCE TO RELATED APPLICATION

This application claims priority to and the benefit of European Community Plant Variety Office application filed on Jul. 5, 2016, Application No. 20161699, the entire contents of which are incorporated herein by reference for all purposes.

BACKGROUND OF THE NEW PLANT

The present invention comprises a new and distinct variety of lavender, botanically known as *Lavandula stoechas*, and hereinafter referred to by the variety name 'KLELV15115'. 'KLELV15115' originated from a cross-pollination conducted in November 2008 in Cobbitty, New South Wales, Australia between the proprietary female lavender variety 'LS901' (unpatented), and the proprietary male lavender variety 'LS903' (unpatented).

The seeds from the cross were sown and plants were grown for evaluation, where an individual plant designated 'KLELV15115' was selected from the group of plants in Cobbitty, New South Wales, Australia in September 2009.

In January 2010, 'KLELV15115' was first vegetatively propagated by stem cuttings in Cobbitty, NSW, Australia. 'KLELV15115' was found to reproduce true to type in successive generations of asexual propagation via vegetative stem cuttings.

SUMMARY

The following are the most outstanding and distinguishing characteristics of this new variety when grown under normal horticultural practices in Cobbitty, New South Wales, Australia.

1. Dark purple terminal bracts; and
2. Very early flowering.

DESCRIPTION OF THE PHOTOGRAPH

This new lavender plant is illustrated by the accompanying photograph which shows the plant's foliage and flowers. The photograph is of a 5 month-old plant grown in a greenhouse in Stuttgart, Germany in October 2015. The colors shown are as true as can be reasonably obtained by conventional photographic procedures.

DESCRIPTION OF THE NEW VARIETY

The following detailed descriptions set forth the distinctive characteristics of 'KLELV15115'. The data which define these characteristics were collected from asexual reproductions carried out in Cobbitty, New South Wales, Australia. Data was collected on four-month-old plants grown in a greenhouse in Cobbitty, New South Wales, Australia in November 2016. Color references are to The R.H.S. Colour Chart of The Royal Horticultural Society of London (R.H.S.), 5$^{th}$ edition (2007).

Classification:
- *Botanical.*—*Lavandula stoechas.*
- *Common.*—Lavender.
- *Designation.*—'KLELV15115'.

Parentage:
- *Female parent.*—The proprietary female lavender variety 'LS901' (unpatented).
- *Male parent.*—The proprietary male lavender variety 'LS903' (unpatented).

Plant:
- *Propagation type.*—Vegetative stem cuttings.
- *Time to initiate roots.*—10 to 12 days.

*Time to produce a rooted cutting.*—19 to 22 days.
*Root description.*—Fine, fibrous and RHS 155C.
*Rooting habit.*—Free branching.
*Plant habit.*—Compact and upright.
*Growth rate.*—Fast.
*Vigor.*—Moderate.
*Plant height.*—34 cm.
*Plant diameter or spread.*—30 cm.

Lateral branches:
*Quantity of lateral branches.*—25 to 30.
*Length.*—13 cm.
*Diameter.*—0.25 cm.
*Stem internode length.*—1.1 cm.
*Number of internodes per branch/stem.*—9 to 12.
*Texture.*—Pubescent.
*Color.*—Juvenile RHS 138B; Mature RHS 138C.
*Stem shape.*—Quadangular.
*Strength.*—Strong.

Foliage:
*Arrangement.*—Opposite.
*Leaf type.*—Simple.
*Quantity per main branch.*—16 to 18 (pairs) fully expanded.
*Length.*—3.1 cm.
*Width.*—0.32 cm.
*Shape.*—Lanceolate.
*Apex.*—Acute.
*Base.*—Truncate.
*Attachment.*—Sessile.
*Margin.*—Entire.
*Leaf fragrance.*—Very strong lavender scent.
*Texture* (*both surfaces*).—Pubescent.
*Immature leaf color* (*both surfaces*).—RHS 191C.
*Mature leaf color* (*both surfaces*).—RHS 191B.
*Venation pattern.*—Pinnate.
*Venation color* (*both surfaces*).—RHS 191B.
*Petiole.*—Absent.

Flowers:
*Form.*—Small single flower in compact verticillasters arranged in spikes.
*Number of rows of flowers.*—9.
*Number of flower spikes per lateral stem.*—1.
*Average number of flowers per spike.*—Approximately 65.
*Inflorescence length* (*excluding terminal bracts*).—3.5 cm.
*Inflorescence width* (*excluding terminal bracts*).—1.8 cm.
*Flower longevity.*—Around 12 days.
*Self-cleaning or persistent.*—Self-cleaning.
*Fragrance.*—Absent.
*Natural flowering season.*—Spring to summer and autumn in Sydney Australia.
*Position of flowers relative to the foliage.*—Moderately above.

Flower buds:
*Length.*—0.5 cm.
*Diameter.*—0.15 cm.
*Shape.*—Oblong.
*Color.*—RHS 93A.
*Rate of opening.*—High.

Corolla:
*Shape.*—Salverform.
*Quantity of petals.*—5.
*Petals fused or unfused.*—Petals fused into a tube.
*Petal length.*—0.5 cm.
*Petal width.*—0.2 cm.
*Petal shape.*—Ovate.
*Petal apex.*—Rounded.
*Petal base.*—Fused.
*Petal margin.*—Entire.
*Petal texture* (*both surfaces*).—Glabrous.
*Petal color, immature.*—Upper surface: RHS N89A. Lower surface: RHS N89B.
*Petal color, mature.*—Upper surface: RHS N89B. Lower surface: RHS N88C.

Calyx:
*Quantity of sepals and arrangement.*—5, fused into a campanulate tube.
*Calyx shape.*—Flattened tube.
*Calyx length.*—0.3 cm.
*Calyx width.*—0.75 cm.
*Sepal texture* (*both surfaces*).—Tomentose.
*Sepal color* (*both surfaces*).—RHS 145B; base close to RHS 145C.
*Sepal shape.*—Lanceolate.

Terminal bracts:
*Quantity.*—4 to 5.
*Attitude of angle of attachment.*—10 to 15 degrees from the top of the inflorescence.
*Length.*—3.1 cm
*Width.*—1.2 cm.
*Form.*—Petaloid.
*Margin.*—Entire.
*Texture* (*both surfaces*).—Smooth.
*Shape.*—Oblanceolate.
*Apex.*—Acute.
*Base.*—Oblique.
*Venation pattern.*—Reticulate.
*Venation color.*—RHS 83A.
*Duration on plant.*—8 to 12 weeks with good color.
*Self-cleaning or persistent.*—Persistent.
*Color* (*both surfaces*).—RHS 83B.

Peduncles:
*Length.*—3.5 cm to 4.5 cm.
*Diameter.*—0.25 cm.
*Strength.*—Moderate.
*Texture.*—Pubescent.
*Color.*—RHS 138B.
*Aspect.*—Straight.

Reproductive organs:
*Stamens.*—Quantity per flower: 4. Filament length: 0.25 cm. Filament color: RHS 75C. Anther length: 0.05 cm. Anther diameter: 0.03 cm. Anther color: RHS N155A. Pollen: Not observed.
*Pistils.*—Quantity per flower: 1. Pistil length: 0.35 cm. Style length: About 0.3 cm. Style color: RHS 75C. Stigma shape: Club-shaped. Stigma length: 0.05 cm. Stigma color: RHS N89B. Ovary: Minute and immeasurable.

Fruit and seed set: None observed.
Disease and pest/insect resistance: None observed.

COMPARISON WITH PARENTAL LINES AND KNOWN VARIETY

'KLELV15115' is distinguished from its parents as described in Table 1.

TABLE 1

| Comparison with Parental Lines | | | |
|---|---|---|---|
| Characteristic | 'KLELV15115' | Female parent 'LS901' | Male parent 'LS903' |
| Earliness | Very early | Early | Medium |
| Branch | Well | Medium | Well |
| Color of terminal bracts | Dark purple | Purple | Dark Purple |

When 'KLELV15115' is compared to the commercial lavender 'Madrid Purple' (patent status unknown), differences between the varieties are described in Table 2.

TABLE 2

| Comparison with Commercial Variety | | |
|---|---|---|
| Characteristic | 'KLELV15115' | 'Madrid Purple' |
| Earliness | 1 to 2 weeks earlier than 'Madrid Purple' | Late |
| Branch | Well | Average |

I claim:

1. A new and distinct variety of lavender plant designated 'KLELV15115' as illustrated and described herein.

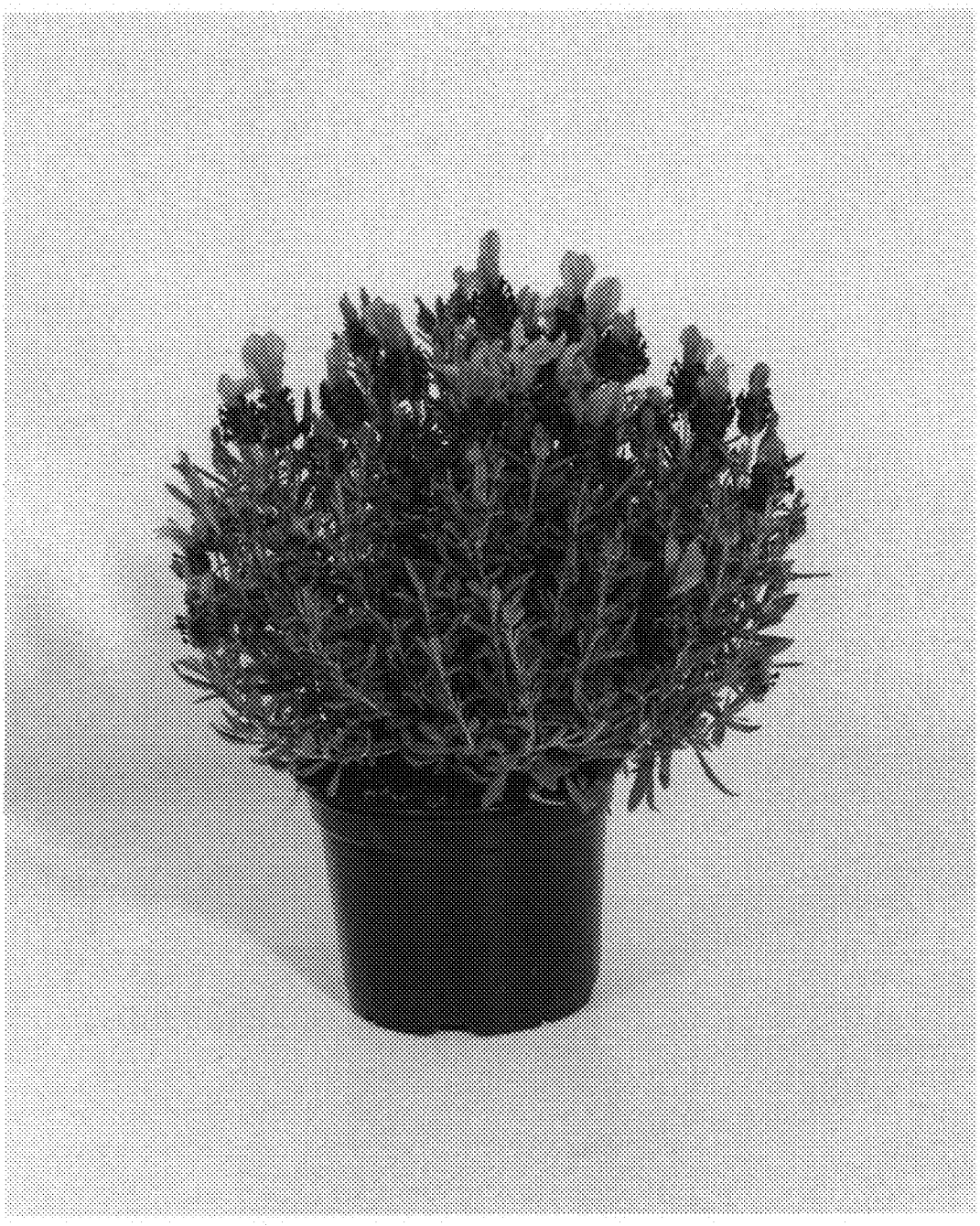

* * * * *